United States Patent [19]

Argenson et al.

[11] Patent Number: 5,702,452
[45] Date of Patent: Dec. 30, 1997

[54] SPINAL OSTEOSYNTHESIS DEVICE WITH MEDIAN HOOK AND VERTEBRAL ANCHORING SUPPORT

[75] Inventors: Claude Argenson; Ferdinand de Peretti; Istvan Hovorka, all of Nice, France

[73] Assignee: Sofamor S.N.C., Paris, France

[21] Appl. No.: 589,849

[22] Filed: Jan. 22, 1996

[30] Foreign Application Priority Data

Jan. 23, 1995 [FR] France .................................. 95 00732

[51] Int. Cl.$^6$ .................................................. A61F 2/44
[52] U.S. Cl. ............................................................ 623/17
[58] Field of Search ................................. 623/17; 606/61

[56] References Cited

U.S. PATENT DOCUMENTS

| | | | |
|---|---|---|---|
| 4,433,677 | 2/1984 | Ulrich et al. | 128/69 |
| 4,773,402 | 9/1988 | Asher et al. | 128/69 |
| 5,007,909 | 4/1991 | Rogozinski | 606/61 |
| 5,201,734 | 4/1993 | Cozad et al. | 606/62 |
| 5,261,907 | 11/1993 | Vignaud et al. | 606/60 |
| 5,368,594 | 11/1994 | Martin et al. | 606/61 |
| 5,387,212 | 2/1995 | Yuam et al. | 606/61 |
| 5,498,263 | 3/1996 | DiNello et al. | 606/61 |

FOREIGN PATENT DOCUMENTS 2645427  11/1990  France .
2659225  9/1991   France .

Primary Examiner—David Isabella
Assistant Examiner—John M. Black
Attorney, Agent, or Firm—Woodard, Emhardt, Naughton Moriarty & McNett

[57] ABSTRACT

Spinal osteosynthesis device comprising, for one and the same vertebra, a hook (12), two vertebral bearing means associated with the said hook, the latter being adapted so as to be able to bear on the median portion of the vertebral posterior arch between two longitudinal rods (7) of the said device, this hook being provided with transverse means of connection (28) between the hook and the longitudinal rods, with the possibility of adjustment, in a sagittal plane from front to back and from top to bottom, and in a frontal plane from left to right, between the rods and the said hook. The hook (12) and the two anchoring screws or hooks afford three bearing points on the same vertebra, and this avoids having to equip the stage above. Moreover, this hook can be put in place, at the end of a surgical intervention, at the desired stage and at any level chosen by the surgeon, while at the same time permitting an appreciable saving in the time taken for it to be put into place compared with the earlier systems.

19 Claims, 7 Drawing Sheets

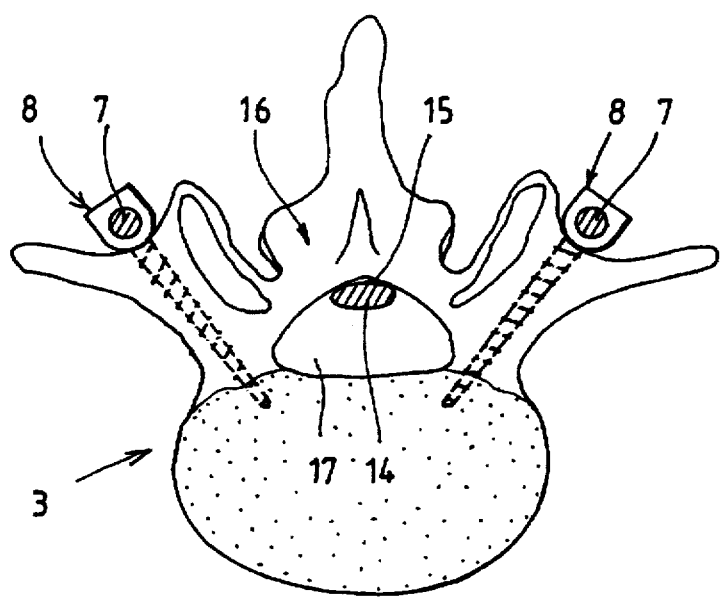
FIG.3
FIG.4
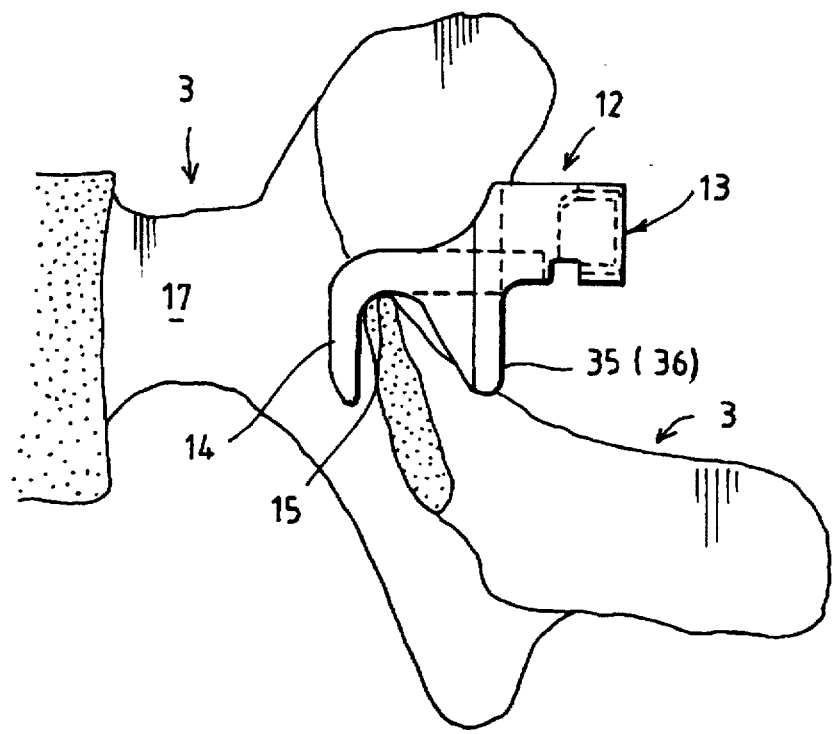

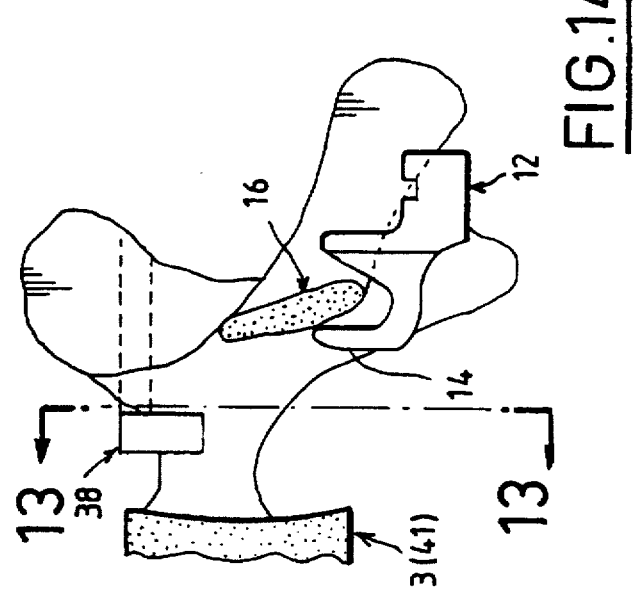
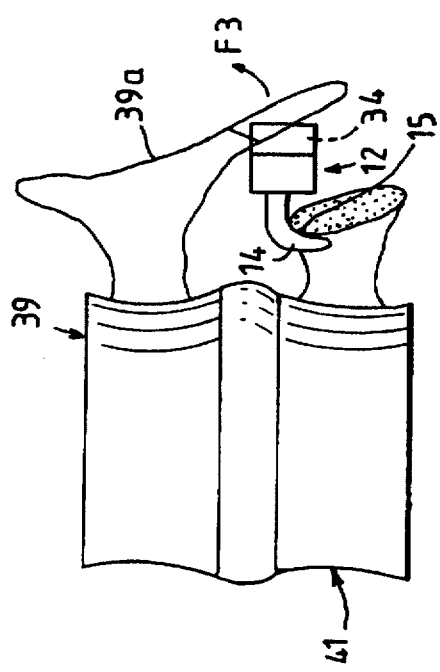
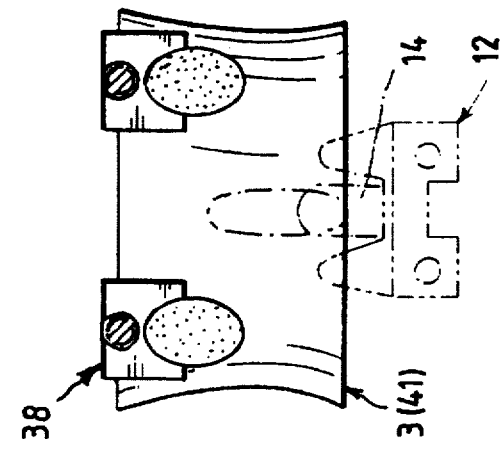

SPINAL OSTEOSYNTHESIS DEVICE WITH MEDIAN HOOK AND VERTEBRAL ANCHORING SUPPORT

BACKGROUND OF THE INVENTION

The present invention relates to a spinal osteosynthesis device of the type comprising two longitudinal rods which extend over the entire length of the vertebral segment to be equipped and which pass through the bodies of vertebral anchoring members, such as pedicle screws.

This device is generally provided with transverse connection systems between the rods. In addition, this instrumentation is frequently completed with hooks which are mounted at the ends of the longitudinal rods and whose curved end portions will bear on the sides of the posterior arch of the subjacent vertebra, consequently penetrating into the medullary canal on either side of the central zone of the posterior arch, and bearing on a lamina of this arch.

These end hooks increase the strength and the rigidity of the instrumentation. However, fitting these hooks in place necessitates equipping an additional vertebra external to the spinal segment concerned in the fitting. Moreover, the duration of this fitting is relatively long and thereby increases all the more the duration of the surgical intervention.

SUMMARY OF THE INVENTION

The aim of the invention is therefore to provide at one and the same time a system for vertebral anchoring and transverse connection between the two longitudinal rods of the spinal osteosynthesis device, which system is designed in such a way as to avoid bearing on an adjacent vertebra not affected by the fitting of the instrumentation, and which can be put in place in a shorter time compared with the hooks which have been used hitherto.

The spinal osteosynthesis device according to the invention comprises, for one and the same vertebra, a hook, two vertebral bearing means associated with the said hook, the latter being adapted so as to be able to bear on the median portion of the vertebral posterior arch between two longitudinal rods of the said device, this hook being provided with transverse means of connection between the hook and the longitudinal rods, with the possibility of adjustment, in a sagittal plane from front to back and from top to bottom, and in a frontal plane from left to right, between the rods and the said hook.

The vertebral bearing means can in particular be pedicle screws or hooks.

Thus, the two hooks which have been used hitherto can be replaced by a single supralaminar median hook of a specific shape adapted to the local anatomy, bearing on the posterior arch in the widest portion of the medullary canal, and not on the sides of the arch, as was the case with the earlier hooks.

The abovementioned transverse means can be brackets which are fixed to the longitudinal rods by any appropriate elements, for example standard hooks of transverse connection devices. The ends of these brackets can be introduced into seats which are formed in the body of the hook. The assembly thereby constitutes a system for vertebral anchoring and for transverse connection between the longitudinal rods.

A system of this kind has the advantage that it is possible to avoid equipping the vertebral stage above, by grouping three bearing points on one and the same stage, with the possibility of adjusting the median hook in relation to the other two bearings. It can further be fitted by the surgeon in a much shorter time than with the pair of hooks used hitherto, for example in about half an hour.

The transverse brackets, which are advantageously bent at a right angle, make it possible to ensure the anchoring of the hook in the supralaminar or sublaminar position (that is to say on one side or other of the lamina of the vertebral arch), on the same vertebra as that equipped with the pedicle anchoring screws or hooks.

According to one embodiment of the invention, the hook includes a blade which is profiled and adapted so as to bear on a central zone of the vertebral posterior arch, in the widest portion of the medullary canal of the spine, the body comprising two lateral parts in which are formed the said bores and a hole for the passage of the corresponding screw, and these two lateral parts are continued via lugs which extend parallel to the blade and form limit stops for the hook on the posterior arch when the blade is introduced into the medullary canal.

Other features and advantages of the invention will be evident from the description which follows and in which reference is made to the attached drawings which illustrate a non-limiting exemplary embodiment thereof.

BRIEF DESCRIPTION OF THE DRAWINGS

FIG. 3 is an elevation of the vertebra in FIG. 2 in the direction of the arrow K, showing the bearing zone of the blade of the hook of the system in FIG. 2, and also the pedicle anchoring points of the equipment used.

FIG. 4 is a schematic longitudinal elevation, on an enlarged scale, of the vertebra in FIGS. 2 and 3, and also of the median hook of the associated vertebral anchoring system.

FIG. 12 is a schematic lateral elevation similar to FIG. 4, on a reduced scale, and showing the position of the median anchoring hook in relation to the spinous process of a thoracic vertebra adjacent to that on which the hook is fitted.

FIG. 13 is a partial sectional view in the direction of 13 in FIG. 14, showing three bearing points on a vertebra, one of which is formed by the blade of the hook according to the invention in the sublaminar position.

FIG. 14 is a lateral elevation, with sectioning of the vertebra, of the sublaminar hook and of pedicle screws.

DESCRIPTION OF THE PREFERRED EMBODIMENT

Figure 1:
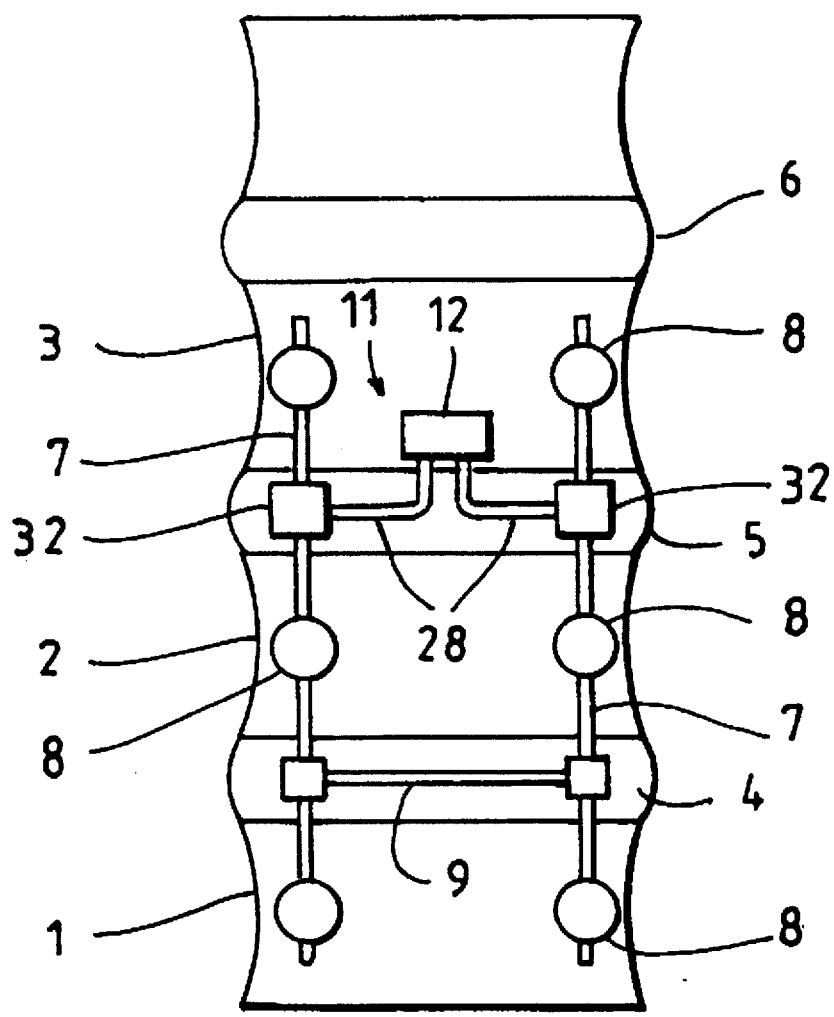
FIG. 1 is a schematic elevation of spinal osteosynthesis equipment put in place on a segment of the spine for the correction of a deviation such as scoliosis, one end of this equipment being provided with a system for vertebral anchoring and for transverse connection according to the invention.

The osteosynthesis equipment which is represented schematically in FIG. 1 extends over a vertebral segment consisting of three vertebrae 1, 2, 3, joined by vertebral discs 4, 5, 6, and comprises two longitudinal rods 7, 8 which are anchored in the vertebral bodies at regular intervals, in a manner known per se using pedicle screws 8 which are represented schematically.

The equipment can be completed with one or more transverse connection devices (TCD) of a type known per se, such as the device 9 connecting the rods 7. These TCD can be for example, of the type which is described in French Patents 2,645,427 of 11 Apr. 1989 and 2,659,225 of 8 Mar. 1990.

The equipment is also provided with a system for vertebral anchoring 11 and for transverse connection between the rods 7, which system is fitted on one of the end vertebrae of the equipped spinal segment, for example vertebra 3 in the example in FIG. 1. This anchoring system will be described in detail, with reference being made more particularly to FIGS. 2 to 8.

It comprises, in the first instance, a median hook 12 consisting of a body 13 and of a longitudinal median blade 14 which is profiled and adapted so as to be able to bear on a central zone 15 of the vertebral posterior arch 16, in the widest portion of the medullary canal 17 of the spine (FIG. 3). The body 13 consists of two lateral parts 18, 19 in which longitudinal bores 21, 22 are formed, their longitudinal axes being parallel to the longitudinal median plane P of the central blade 14 and being symmetrical with the latter. Opening perpendicularly into these bores 21, 22 are tapped holes 23, 24 which are adapted to receive screws 25, 26 for locking or fixing, respectively, to the body 13 the cylindrical ends 20 of bent brackets 28 for connection of the hook 12 to the longitudinal osteosynthesis rods 7.

Each bracket 28 thus consists of a small transverse bar 29 with, for example, a rectangular cross-section (FIGS. 2 and 8) and with a cylindrical end 20 which is bent at a right angle to the small bar 29. The diameter of the end 20 allows it to be introduced into the corresponding bore 21 or 22. These cylindrical parts 20 are connected to the small bars 29 via transition zones 31 whose cross-section is practically constant so as not to create a zone of reduced strength. The length of the cylindrical ends 20, whose surface is advantageously roughened 20a(knurling, diamond points . . .), is preferably substantially greater than that of the associated bores 21, 22 in order to permit an adjustment of the longitudinal position of the hook 12 in a direction parallel to the rods 7, as is illustrated by the double arrow F in FIG. 2.

The small bars 29 can be secured via their ends to the longitudinal rods 7 by any appropriate means known per se, such as hooks 32 which include a channel in which the end of the corresponding small bar 29 will sit. A screw 33 screwed into the body of the hook 32 locks the small bar 29 on the rod 7, which is itself received in the blade 30 of the hook 32.

Figure 5:
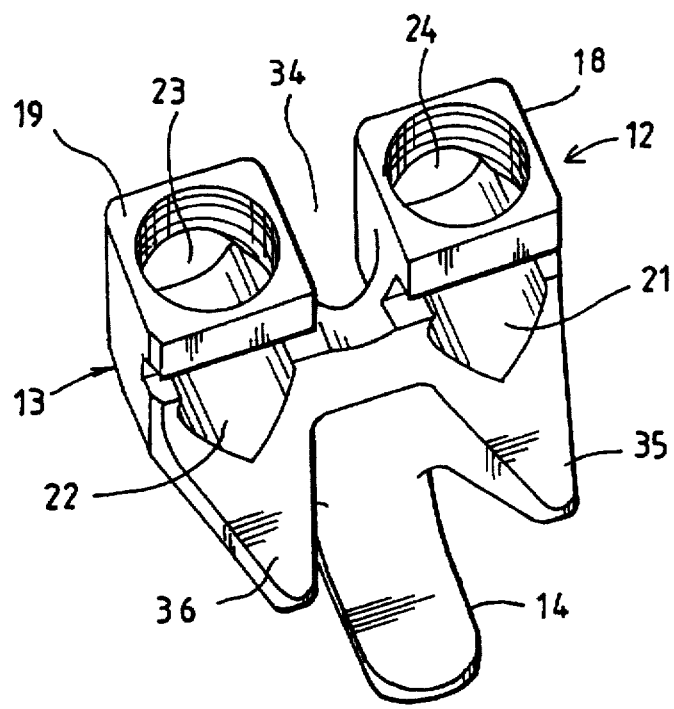
FIG. 5 is a perspective view, on an enlarged scale, of the hook in FIGS. 2 and 4.
Figure 6:
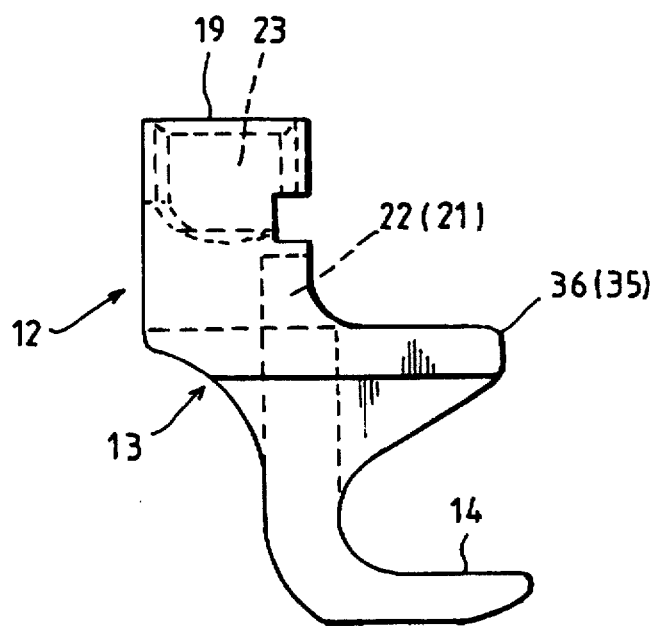
FIG. 6 is a lateral elevation corresponding to FIG. 5.

Referring in particular to FIGS. 5 and 6, it will be seen that the two lateral parts 18, 19 of the median hook 12 are separated by a longitudinal central channel or recess 34 and are each continued via a longitudinal lug 35, 36 extending on either side of the median blade 14 in longitudinal directions which are parallel to those of the blade 14.

Figure 7:
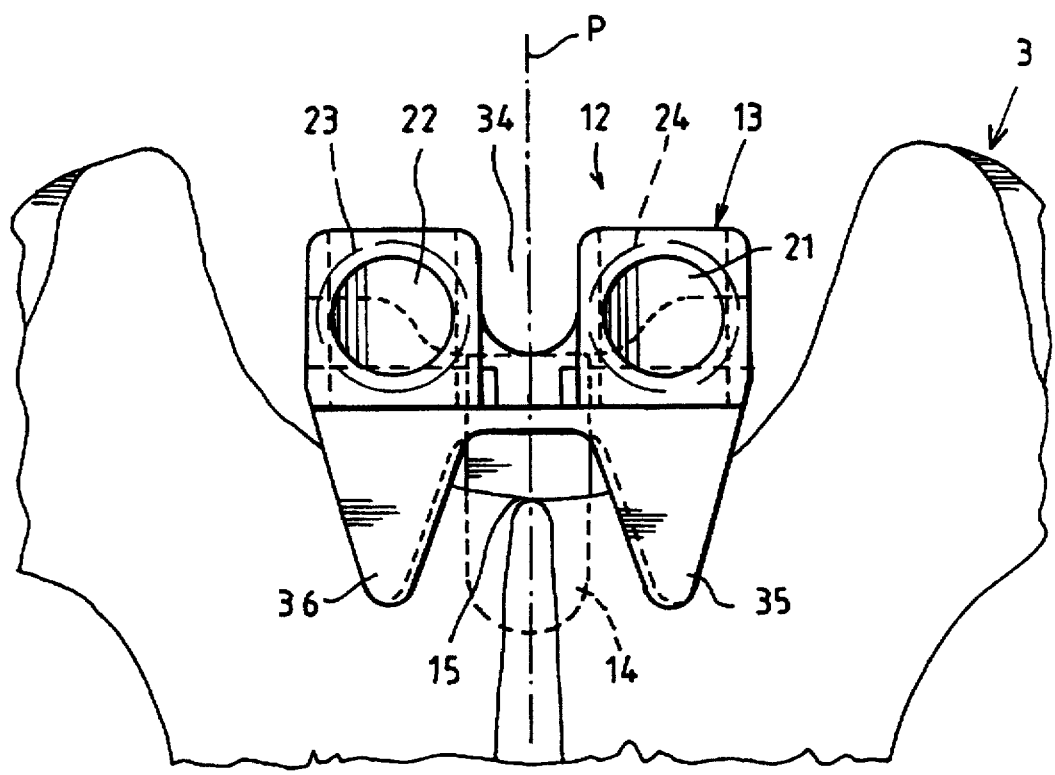
FIG. 7 is a plan view of the hook in FIG. 5 and a partial view of the corresponding vertebra.
Figure 8:
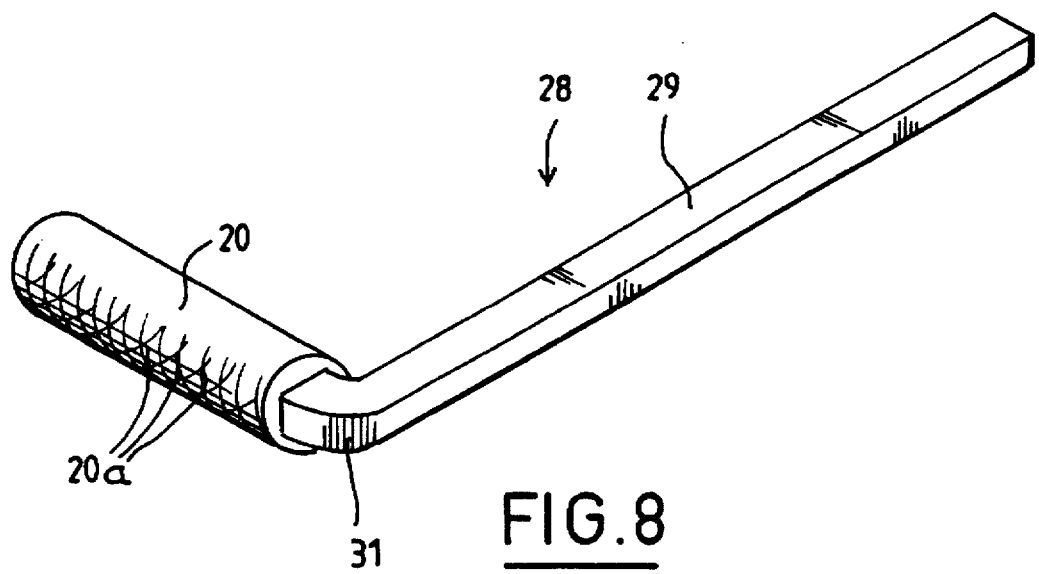
FIG. 8 is a perspective view, on an enlarged scale, of a bent bracket of the anchoring system in FIG. 2.

The lugs 35, 36 are profiled so as to be able to adapt to the local anatomy of the posterior arch on either side of the central bearing zone of the blade 14, in order to form, for the latter, limit stops which prevent penetration of the blade 14 into the medullary canal beyond a suitable point (FIG. 7).

The positioning of the system for vertebral anchoring and for transverse connection which has just been described is carried out in the following manner: the surgeon first passes the respective cylindrical end parts 20 of the brackets 28 into the bores 21, 22, placing these brackets in the desired longitudinal position, and he then effects an initial screwing of the screws 25, 26 in order to hold the ends 20 in place. Secondly, the ends of the small bars 29 are successively introduced into the channels of the hooks 32 until their ends 29a project slightly from the hooks through slots in the latter, and the surgeon then carries out the screwing of the screws 33 in order to effect a provisional blocking of the whole device on the osteosynthesis rods 7.

Figure 10:
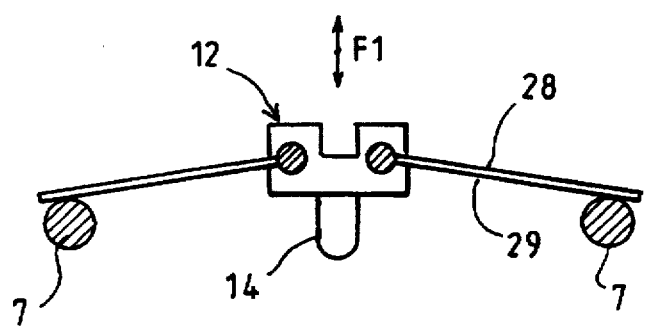
FIGS. 10 and 11 are rear elevation views, essentially to scale, of the anchoring system in FIG. 2, showing the possibilities of deflection of the hook in translation and in rotation in a transverse plane perpendicular to the longitudinal rods.
Figure 11:
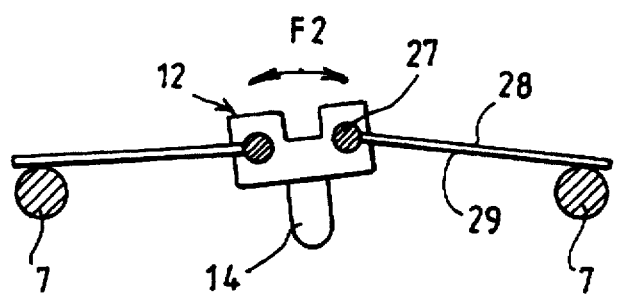

At this stage, a final adjustment can be made in two directions, as is illustrated in FIGS. 10 and 11, that is to say in a sagittal plane from front to rear and from top to bottom, and in a frontal plane from left to right. It will be seen from FIG. 10 that since the locking of the ends 20 in the screws 25, 26 is not complete, there remains a possibility of articulation of the hook 12 on its ends 20 in a transverse plane perpendicular to the plane of the rods 7 (double arrow F1, FIG. 10). Likewise, the median hook 12 can be tilted on one side or the other about one or other of the ends 20 in order to adjust the position of the hook 12 to the local anatomy of the patient, by rotation about the cylindrical ends 20 (FIG. 11, arrow F2).

Figure 2:
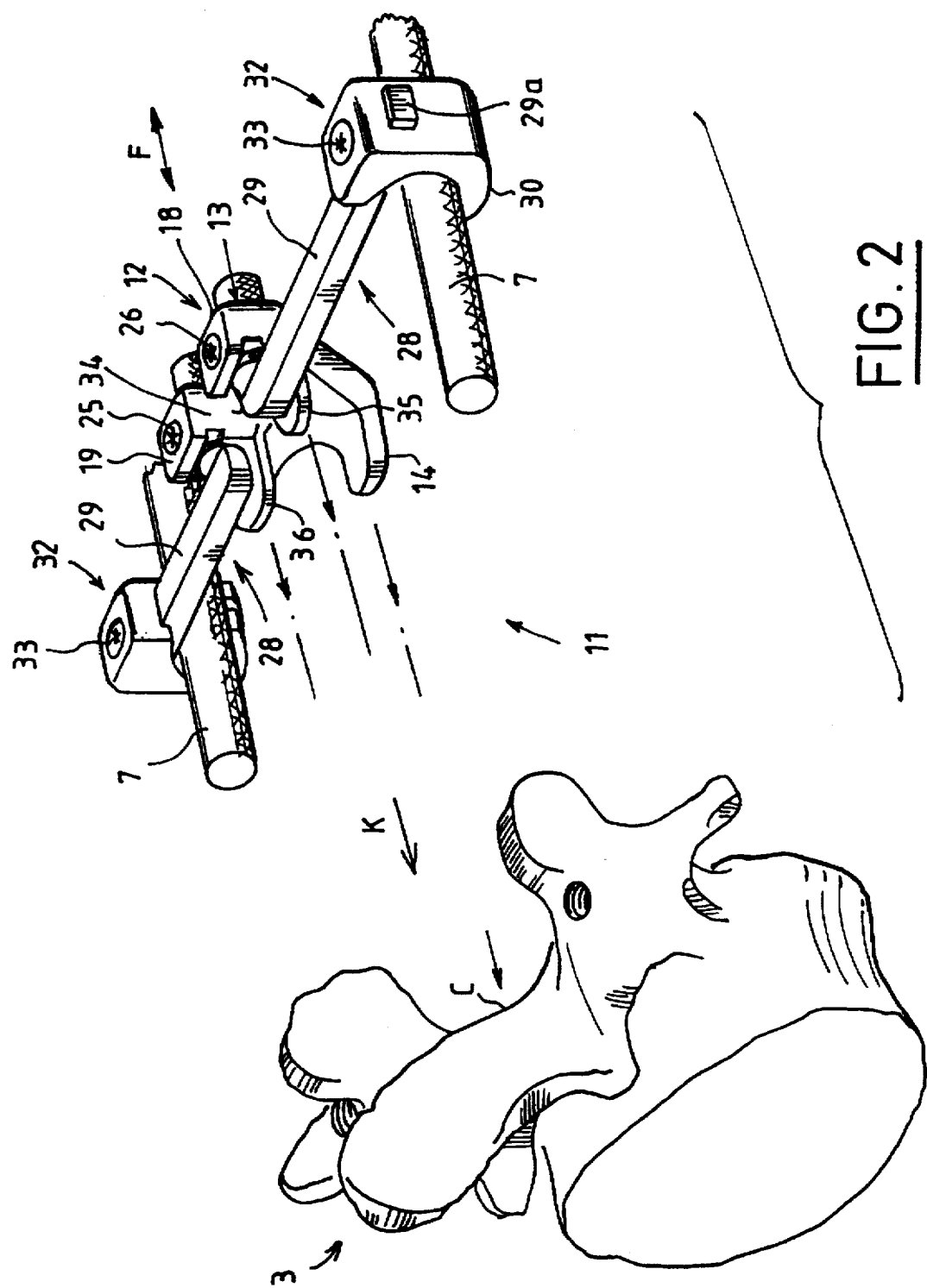
FIG. 2 is a partial perspective view, on an enlarged scale, of the anchoring and transverse connection system in FIG. 1, and also of the corresponding vertebra on which the hook of this system is anchored.

After final positioning of the median hook 12 in the longitudinal direction (arrow F), in the vertical direction (arrow F1, assuming that the plane defined by the rods 7 is horizontal), and finally about the cylindrical parts 20, the screws 25, 26 and 33 can be definitively locked in order to hold the blade 14 securely bearing against the central zone 15 of the posterior arch 16 (FIGS. 2, 3 and 12). The penetration into the medullary canal is arrested by the safety stops 35, 36 bearing against the sides of the posterior arch 16 on either side of the central zone 15.

This bearing via the blade 14 of the median hook 12 can be either supralaminar (FIGS. 2 and 3) or sublaminar, as is represented in FIGS. 13 and 14. In both cases, the hook 12 provides, together with the two means of pedicle anchoring on one and the same vertebra, either by pedicle screws 8 (FIG. 3) or by pedicle hooks 38 (FIGS. 13 and 14), a system of anchoring at three points for the vertebra thus equipped, for example vertebra 3. A device for bearing at three points on one and the same vertebra is thus obtained in which the median hook 12 is placed in opposition to the pedicle bearing means in order to stabilize the vertebra.

For certain vertebrae, in particular the thoracic vertebrae 39 (FIG. 12), the recess 34 serves as a channel for receiving the spinous process 39a of the said vertebra once the hook 12 has been put in place on the contiguous vertebra 41. The spinous process 39a is first lifted or sectioned by the surgeon (arrow F3) in order to facilitate the positioning of the hook 12, after which the spinous process is returned to its original position or joined together. The spinous process 39a then engages in the longitudinal channel 34.

Figure 9:
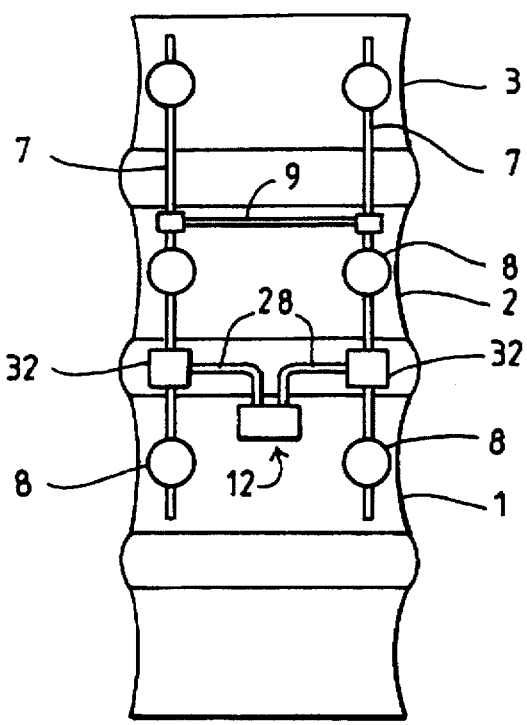
FIG. 9 is a partial schematic elevation analogous to FIG. 1 and representing an alternative embodiment of the vertebral anchoring system.

In the alternative embodiment represented in FIG. 9, the brackets 28, and more precisely their end parts 27, are oriented in a manner which is the opposite of that represented in FIG. 1, that is to say these ends 27 are engaged in the bores 21, 22 via the entrance of the latter opposite that shown in FIG. 1 and 2. The small bars 29 are thus offset longitudinally on the other side of the body 13, the desired result being otherwise evidently the same. It is also possible to introduce one of the ends 27 via an entrance of the bore 21 or 22 opposite the one through which the other end 27 is introduced into the associated bore.

In the various possible embodiments of the hook and of the vertebral anchoring system incorporating this hook, the invention affords the following advantages (in addition to the advantages which have already been mentioned):

The anchoring system at the same time serves as a transverse connection system complementing those, such as 9, which have already been fitted on the osteosynthesis equipment, and thereby reinforces the strength of the assembly.

The invention makes it possible to obtain three bearing points on the same vertebra, namely the bearing by the blade 14 of the median hook 12 and the two pedicle bearings by the pedicle screws 8, or the pedicle hooks 38. This therefore obviates equipping the adjacent vertebra which is not affected by the osteosynthesis equipment, which fact represents a substantial advantage in relation to the prior art cited hereinabove.

The fitting of the hook 12 according to the invention with its lateral brackets 28 and its securing means can be effected, as has already been indicated, in a much shorter time than that which was hitherto required by the surgeon.

By virtue of the articulations formed between the hook 12 and the brackets 28 by the cylindrical ends 20 and their bores 21, 22, the hook 12 can be adapted to all the particular anatomical situations of the small bars 29 in relation to the spine, since this hook 12 can rise or fall, tilting the small bars 29, and can also be displaced axially to make up for anatomical particularities.

The posterior lugs 35, 36 advantageously constitute limit stops for the blade 14, which prevent the latter from penetrating into the medullary canal 17 beyond the point which has been assigned to it, and this avoids any risk of damage to the spinal cord.

The hook 12 and the transverse brackets 28 can be put in place at the end of the surgical intervention, at the desired vertebral stage and at any level, it being possible for this choice to be made by the surgeon during the operation.

The time taken to put a TCD such as 9 in place is practically equal to the time taken for putting the hook 12 in place, which corresponds to a time saving of approximately 30 minutes compared with the earlier system with two hooks plus a transverse connection device. Indeed, it is important to emphasize that the system according to the invention also serves as a transverse connection device, which is not the case with the hooks of the known earlier devices. For this reason, the invention makes it possible, by fitting a single hook, to provide at one and the same time a vertebral anchoring at the level of the posterior arch and also a transverse connection, and thus to dispense with the fitting of an adjacent transverse connection device.

The device provided by the invention does not require specific ancillary parts, those of the existing instrumentation being capable of being used without difficulty.

The indications for the device according to the invention are the following:

a) Whenever it is wished to complete a fitting with a hook, that is to say in traumatology, for the treatment of scoliosis and for the treatment of osteoporosis.

b) Whenever it is wished to complete a fitting with screws and hooks.

The invention advantageously makes it possible to obtain vertebral clamps by virtue of the three bearings suitably arranged as indicated hereinabove, the blade 14 being either in a supralaminar position or in a sublaminar position (in the latter case the hook 12 is of course suitably dimensioned and adapted). The clamp which is thus obtained offers the surgeon the possibility of making various corrections and ensures better mechanical stability of the equipped vertebra.

As an alternative, the bores 21, 22 can be formed differently, for example consisting of spherical seats which receive end spheres of the brackets 28.

We claim:

1. A spinal osteosynthesis device, comprising:
two longitudinal rods configured for fixation along opposite sides of a patient's spine;
a transverse connection means extending between said rods, said connection means being configured for placement over a vertebra of the patient's spine, said connection means including a hook and a pair of brackets engaging said rods to position said hook generally midway between said rods, said hook having a blade configured to engage a median portion of a vertebral posterior arch of the vertebra.

2. The device according to claim 1, wherein said connection means includes an adjustment means for adjusting a position of said hook relative to a sagittal plane and a frontal plane.

3. The device according to claim 1, wherein said connection means further includes a pair of lugs configured to limit penetration of said blade when said blade bears against the median portion of the vertebral posterior arch.

4. The device according to claim 1, wherein said connection means includes a body with two lateral parts defining a longitudinal recess therebetween, said recess being configured to receive a spinous process of the vertebra.

5. The device according to claim 1, wherein said brackets each include a bar, said bar has a rod engaging end with a generally rectangular cross-section and a hook engaging end with a generally circular cross-section wherein a rod hook is configured to engage the rod engaging end of the bar.

6. The device according to claim 5, wherein said bar is bent with a generally constant cross-sectional area from said rod engaging end to said hook engaging end, and said bar has a generally roughened surface at said hook engaging end.

7. The device according to claim 6, wherein said rod engaging end of said bar is locked to a corresponding one of said rods with said rod hook.

8. A spinal osteosynthesis device, comprising:
a pair of longitudinal rods configured for fixation along opposing sides of a patient's spine;
a transverse connector fixed to each of said rods and extending therebetween, said connector being configured for placement over a vertebra of the patient's spine, said connector including a hook and a pair of brackets, said hook adjustably positioned between said rods by said pair of brackets, said hook being adapted to bear on a median portion of a vertebral posterior arch of the vertebra, said brackets each engaging said hook and a corresponding one of said rods.

9. The device according to claim 8, wherein said hook includes a blade and a body, and said body defines a pair of bores and a pair of tapped holes intersecting said bores.

10. The device according to claim 8, wherein said hook further includes a pair of lugs configured to limit penetration of said blade when said blade bears against the median portion of the vertebral posterior arch.

11. The device according to claim 9, wherein said body has two lateral parts defining a longitudinal recess therebetween, said recess being configured to receive a spinous process of the vertebra.

12. The device according to claim 8, wherein said brackets each include a bar, said bar has a rod engaging end with a generally rectangular cross-section and a hook engaging end with a generally circular cross-section, wherein a rod hook is configured to engage the rod engaging end of the bar, said bars are each bent, and each bar has a generally roughened surface at said hook engaging end.

13. A transverse connection device for extending between a first rod and a second rod of a spinal osteosynthesis system, comprising:

a first bracket having a first rod engaging end configured to engage the first rod and a first bore engaging end;

a second bracket having a second rod engaging end configured to engage the second rod and a second bore engaging end;

a vertebral hook with a body and a blade, said blade being configured to engage a median portion of a vertebral posterior arch of a patient's vertebra, said body defining:

a first bore configured for engagement by said first bore engaging end of said first bracket, a second bore being configured for engagement by said second bore engaging end of said second bracket, a first tapped hole intersecting said first bore, a second tapped hole intersecting said second bore;

a first screw configured to engaged said first tapped hole and bear against said first bore engaging end when engaged in said first bore;

a second screw configured to engage said second tapped hole and bear against said second bore engaging end when engaged in said second bore; and, whereby said vertebral hook is adjustably positioned between the first and second rods along a sagittal plane and a frontal plane when said first bracket engages the first rod and said first bore to extend therebetween, said second bracket engages the second rod and said second bore to extend therebetween, said first screw engages said first tapped hole to bear against said first bore engaging end of said first bracket, and said second screw engages said second tapped hole to bear against said second bore engaging end of said second bracket.

14. The device according to claim 13, wherein said body includes two lateral parts defining a longitudinal recess therebetween, said recess being configured to receive a spinous process of the patient's vertebra.

15. The device according to claim 13, wherein:

said first bracket includes a first rod hook at said first rod engaging end and a first bar; and said second bracket includes a second rod hook at said second rod engaging end and a second bar.

16. The device according to claim 13, wherein said vertebral hook further includes a pair of lugs configured to limit penetration of said blade when said blade bears against the median portion of the vertebral posterior arch.

17. The device according to claim 16, wherein:

said first rod hook defines a first tapped bore and includes a first set screw configured to engage said first tapped bore and bear against said first bar to clamp said first rod hook, said first bar, and the first rod together; and said second rod hook defines a second tapped bore and includes a second set screw configured to engage said second tapped bore and bear against said second bar to clamp said second rod hook, said second bar, and the second rod together.

18. The device according to claim 17, wherein:

said first bar has a generally rectangular cross-section at said first rod engaging end and changes to a generally circular cross-section at said first bore engaging end; and said second bar has a generally rectangular cross-section at said second rod engaging end and changes to a generally circular cross-section at said second bone engaging end.

19. The device according to claim 18, wherein:

said first bar is bent and has a generally roughened surface at said first bore engaging end;

said second bar is bent and has a generally roughened surface at said second bore engaging end.

* * * * *